(12) United States Patent
Falcó et al.

(10) Patent No.: US 8,993,562 B2
(45) Date of Patent: *Mar. 31, 2015

(54) IMIDAZO[1,2-B]PYRIDAZINES, PROCESSES, USES, INTERMEDIATES AND COMPOSITIONS

(75) Inventors: José Luís Falcó, Barcelona (ES); Albert Palomer, Barcelona (ES); Antonio Guglietta, Barcelona (ES)

(73) Assignee: Ferrer Internacional, S.A., Barcelona (ES)

(*) Notice: Subject to any disclaimer, the term of this patent is extended or adjusted under 35 U.S.C. 154(b) by 155 days.

This patent is subject to a terminal disclaimer.

(21) Appl. No.: 13/282,926

(22) Filed: Oct. 27, 2011

(65) Prior Publication Data

US 2012/0040979 A1 Feb. 16, 2012

Related U.S. Application Data

(62) Division of application No. 12/225,740, filed as application No. PCT/EP2007/052988 on Mar. 28, 2007, now Pat. No. 8,153,789.

(30) Foreign Application Priority Data

Mar. 29, 2006 (EP) .................................. 06111899

(51) Int. Cl.
*A61K 31/50* (2006.01)
*C07D 413/00* (2006.01)
*C07D 487/04* (2006.01)
*A61P 25/20* (2006.01)
*A61P 25/22* (2006.01)

(52) U.S. Cl.
CPC .................................... *C07D 487/04* (2013.01)
USPC ......... 514/233.2; 514/248; 544/117; 544/236

(58) Field of Classification Search
USPC .................. 544/117, 236; 514/233.2, 248
See application file for complete search history.

(56) References Cited

U.S. PATENT DOCUMENTS

| | | | | |
|---|---|---|---|---|
| 6,248,740 B1 * | 6/2001 | Kawano et al. | ............... | 514/248 |
| 6,627,630 B1 * | 9/2003 | Kawano et al. | ............... | 514/248 |
| 2009/0318410 A1 | 12/2009 | Capraro et al. | | |
| 2011/0301190 A1 * | 12/2011 | Kumke et al. | ............... | 514/302 |

FOREIGN PATENT DOCUMENTS

| | | |
|---|---|---|
| JP | 2002371042 * | 12/2002 |
| WO | WO 89/01333 A | 2/1989 |
| WO | WO 00/23450 A1 | 4/2000 |
| WO | WO 01/34152 A1 | 5/2001 |
| WO | WO 03/076442 A1 | 9/2003 |

OTHER PUBLICATIONS

Abignente et al., Farmaco, Edizione Scientifica (1980), 35(8), 654-73.
Barlin, G. B. et al., "Imidazo[1,2-b]pyridazines. X* Syntheses and Central Nervous System Activities of Some 3-(Acetamido, benzamido, substituted benzamido or dimethylamino)methyl-2-(phenyl or substituted phenyl)-6-(halogeno,alkylthio, alkoxy, phenylthio, pnenoxy, benzylthio or benzyloxy) imidazo[1,2-b]pyridazines", Australian Journal of Chemistry, vol. 45, 1992, pp. 731-749.
Edwards, J. Med. Chem. 39 (1996), pp. 1112-1124.
Engler et al., Bioorg. & Med. Chem Ltrs. (2005), 15(4), 899-903.
Fourie, International J. Pharmaceutics, vol. 279, Issues 1-2, Jul. 26, 2004, pp. 59-66.
Goosen et al., Pharmaceutical Research vol. 19, No. 1, 13-19 (Jan. 2002).
Gyotenluraschi et al., Chem & Pharm. Bull. (2003), 51(2), 122-123.
Kems et al., Drug-Like Properties: Concepts, Structure Design & Methods: from ADME to Toxicity Optimization, (Elsevier, 2008) pp. 92-93.
Leonard, J. Psychosom Res. 1994;38 Suppl 1: 69-87.
Luraschi et al., Farmaco (1995), 50(5), 349-54.
Rautio, Eur. J. Pharm. Sci, 11:157-163 (2000).
Sacchi A et al., "Research on heterocyclic compounds, XLI. 2-Phenylimidazo[1,2-b]pyridazine-3-acetic derivatives: synthesis and anti-inflammatory activity", European Journal of Medicinal Chemistry Editions Scientifique Elsevier, vol. 34, No. 11, Nov. 1999, pp. 1003-1008.
Trapani G, "Novel 2-Phenylimidazo[1,2-a] pyridine Derivatives as Potent and Selective Ligands for Peripheral Benzodiazepine Receptors: Synthesis, Binding Affinity, and in Vivo Studies", Journal of Medicinal Chemistry, American Chemical Society, vol. 42, 1999, pp. 3934-3941.
Vinkers et al., The Open Pharmacol. J., 2010, 4, pp. 1-14.
Wallace et al., Nat. Genet. 2001: 28, pp. 49-52.
Wang et al., Pharmacol Biochem Behay. Feb. 2003; 74(3):573-8.
Office Action dated Aug. 31, 2010 for U.S. Appl. No. 12/225,740.
Office Action dated Nov. 24, 2010 for U.S. Appl. No. 12/225,740.
Office Action dated Jul. 5, 2011 for U.S. Appl. No. 12/225,740.

* cited by examiner

*Primary Examiner* — James O Wilson
*Assistant Examiner* — Cecilia M Jaisle
(74) *Attorney, Agent, or Firm* — Birch, Stewart, Kolasch & Birch, LLP

(57) ABSTRACT

The invention provides novel imidazo[1,2-b]pyridazines of formula (I) and pharmaceutically acceptable salts, polymorphs, hydrates, tautomers, solvates and stereoisomers thereof. Compounds of formula (I) are useful for treating or preventing diseases associated with $GABA_A$ receptors modulation, anxiety, epilepsy, sleep disorders including insomnia, and for inducing sedation-hypnosis, anesthesia, sleep and muscle relaxation.
The invention also provides synthetic procedures for preparing said compounds and certain intermediates, as well as intermediates themselves.

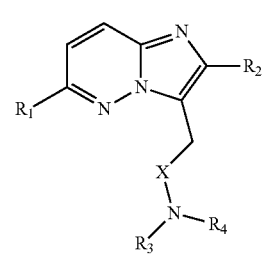

(I)

15 Claims, No Drawings ately by the $\alpha_1$-receptors.

IMIDAZO[1,2-B]PYRIDAZINES, PROCESSES, USES, INTERMEDIATES AND COMPOSITIONS

CROSS REFERENCE FOR RELATED APPLICATIONS

The present application is a 37 C.F.R. §1.53(b) divisional of, and claims priority to, U.S. application Ser. No. 12/225,740, filed Sep. 29, 2008 now U.S. Pat. No. 8,153,789. Application Ser. No. 12/225,740 is a national phase under 35 U.S.C. §371 of International Application No. PCT/EP2007/052988, filed on Mar. 28, 2007. Priority is also claimed to European Application 06111899.8 filed on Mar. 29, 2006. The entire contents of each of these applications is hereby incorporated by reference.

This invention is directed to agents with affinity for $GABA_A$ receptor, specifically to imidazo[1,2-b]pyridazine compounds.

BACKGROUND OF THE INVENTION $GABA_A$ receptor ($\gamma$-aminobutyric acid$_A$) is a pentameric protein which forms a membrane ion channel. $GABA_A$ receptor is implicated in the regulation of sedation, anxiety, muscle tone, epileptogenic activity and memory functions. These actions are due to defined subunits of $GABA_A$ receptor, particularly the $\alpha_1$- and $\alpha_2$-subunits.

Sedation is modulated by the $\alpha_1$-subunit. Zolpidem is characterized by a high affinity for the $\alpha_1$-receptors and its sedative and hypnotic action is mediated by these receptors in vivo. Similarly, the hypnotic action of zaleplon is also mediated by the $\alpha_1$-receptors.

The anxiolytic action of diazepam is mediated by the enhancement of GABAergic transmission in a population of neurons expressing the $\alpha_2$-receptors. This indicates that the $\alpha_2$-receptors are highly specific targets for the treatment of anxiety.

Muscle relaxation in diazepam is mainly mediated by $\alpha_2$-receptors, since these receptors exhibit a highly specific expression in spinal cord.

The anticonvulsant effect of diazepam is partly due to $\alpha_1$-receptors. In diazepam, a memory-impairing compound, anterograde amnesia is mediated by $\alpha_1$-receptors.

$GABA_A$ receptor and its $\alpha_1$- and $\alpha_2$-subunits have been widely reviewed by H. Möhler et al. (J. Pharmacol. Exp. Ther., 300, 2-8, 2002); H. Möhler et al. (Curr. Opin. Pharmacol., 1, 22-25, 2001); U. Rudolph et al. (Nature, 401, 796-800, 1999); and D. J. Nutt et al. (Br. J. Psychiatry, 179, 390-396, 2001).

Diazepam and other classical benzodiazepines are extensively used as anxiolytic agents, hypnotic agents, anticonvulsants and muscle relaxants. Their side effects include anterograde amnesia, decrease in motor activity and potentiation of ethanol effects.

In this context, the compounds of this invention are ligands of $\alpha_1$- and $\alpha_2$-$GABA_A$ receptor for their clinical application in sleep disorders, preferably insomnia, anxiety and epilepsy.

Insomnia is a highly prevalent disease. Its chronicity affects 10% of the population and 30% when transitory insomnia is computed as well. Insomnia describes the trouble in getting to sleep or staying asleep and is associated with next-day hangover effects such as weariness, lack of energy, low concentration and irritability. The social and health impact of this complaint is important and results in evident socioeconomic repercussions.

Pharmacological therapy in the management of insomnia firstly included barbiturates and chloral hydrate, but these drugs elicit numerous known adverse effects, for example, overdose toxicity, metabolic induction, and enhanced dependence and tolerance. In addition, they affect the architecture of sleep by decreasing above all the duration and the number of REM sleep stages. Later, benzodiazepines meant an important therapeutic advance because of their lower toxicity, but they still showed serious problems of dependence, muscle relaxation, amnesia and rebound insomnia following discontinuation of medication.

The latest known therapeutic approach has been the introduction of non-benzodiazepine hypnotics, such as pyrrolo[3,4-b]pyrazines (zopiclone), imidazo[1,2-a]pyridines (zolpidem) and, finally, pyrazolo[1,5-a]pyrimidines (zaleplon). Later, two new pyrazolo[1,5-a]pyrimidines, indiplon and ocinaplon, have entered into development, the latter with rather anxiolytic action. All these compounds show a rapid sleep induction and have less next-day hangover effects, lower potential for abuse and lower risk of rebound insomnia than benzodiazepines. The mechanism of action of these compounds is the alosteric activation of $GABA_A$ receptor through its binding to benzodiazepine binding site (C. F. P. George, The Lancet, 358, 1623-1626, 2001). While benzodiazepines are unspecific ligands at $GABA_A$ receptor binding site, zolpidem and zaleplon show a greater selectivity for $\alpha_1$-subunit. Notwithstanding that, these drugs still affect the architecture of sleep and may induce dependence in long-term treatments.

Some N-imidazo[1,2-b]pyridazin-3-yl-methyl-alkanamides and N-imidazo[1,2-b]pyridazin-3-yl-methyl-benzamides, wherein the phenyl ring from the benzamide group can be optionally substituted, have been disclosed in WO 89/01333.

The compounds of the present invention are structurally related to, but distinct from the compound N,N,6-trimethyl-2-p-tolylimidazo[1,2-a]pyridine-3-acetamide, zolpidem, which is described in U.S. Pat. No. 4,382,938, because of their improved properties as shown in the Detailed Description of the Invention.

Research for new active compounds in the management of insomnia answers an underlying health need, because even recently introduced hypnotics still affect the architecture of sleep and may induce dependence in long-term treatments.

It is therefore desirable to focus on the development of new hypnotic agents with a lower risk of side effects.

SUMMARY OF THE INVENTION

The present invention provides new imidazo[1,2-b]pyridazines which are active versus $GABA_A$ and, particularly, versus its $\alpha_1$- and $\alpha_2$-subunits. Consequently, the compounds of this invention are useful in the treatment and prevention of all those diseases mediated by $GABA_A$ receptor $\alpha_1$- and $\alpha_2$-subunits. Non-limitative examples of such diseases are sleep disorders, preferably insomnia, anxiety and epilepsy. Non-limitative examples of the relevant indications of the compounds of this invention are all those diseases or conditions, such as insomnia or anesthesia, in which an induction of sleep, an induction of sedation or an induction of muscle relaxation are needed.

Thus, the present invention describes a novel class of compounds represented by formula (I):

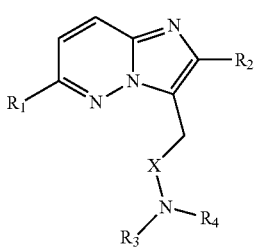

and pharmaceutically acceptable salts, polymorphs, hydrates, tautomers, solvates and stereoisomers thereof, wherein $R_1$ to $R_4$, and Y are defined below, which are ligands of $GABA_A$ receptor.

It is another object of this invention to provide synthetic procedures for preparing the compounds of formula (I), certain intermediates thereof, as well as intermediates themselves. Novel methods of treating or preventing diseases associated with $GABA_A$ receptors modulation such as anxiety, epilepsy and sleep disorders including insomnia, and for inducing sedation-hypnosis, anesthesia, sleep and muscle relaxation by administering a therapeutically effective amount of said compounds are also within the scope of the invention.

DETAILED DESCRIPTION OF THE INVENTION

The present invention relates to novel imidazo[1,2-b]pyridazine compound of formula (I):

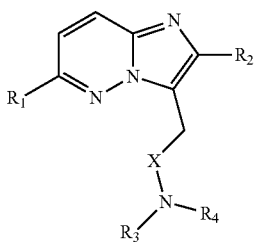

wherein
$R_1$ and $R_2$ are independently selected from the group consisting of hydrogen, linear or branched alkyl($C_1$-$C_6$), alkenyl($C_2$-$C_6$), alkynyl($C_2$-$C_6$), cycloalkyl($C_3$-$C_6$), haloalkyl($C_2$-$C_6$), hydroxy, —O-alkyl($C_1$-$C_6$), phenoxy, —S-alkyl($C_1$-$C_6$), phenylthio, halogen, nitro, cyano, amino, alkylamino($C_1$-$C_6$), dialkylamino($C_1$-$C_6$), pyrrolidinyl, morpholinyl, piperidinyl, N-alkyl($C_1$-$C_6$)piperazinyl, phenyl optionally substituted by 1 to 5 Z groups and heteroaryl optionally substituted by 1 to 5 Z groups; $R_3$ and $R_4$ are independently selected from the group consisting of hydrogen, linear or branched alkyl($C_1$-$C_6$), alkenyl($C_2$-$C_6$), alkynyl($C_2$-$C_6$), cycloalkyl($C_3$-$C_6$), hydroxyalkyl($C_1$-$C_6$), amino, —NH-alkyl($C_1$-$C_6$), —N-dialkyl($C_1$-$C_6$), pyrrolidinyl, morpholinyl, piperidinyl, —N-alkyl($C_1$-$C_6$)piperazinyl, —N-acyl($C_1$-$C_6$)piperazinyl, phenyl optionally substituted by 1 to 5 Z groups and heteroaryl optionally substituted by 1 to 5 Z groups, or both $R_3$ and $R_4$ can form, together with the nitrogen atom to which they are attached, a 5-6 membered heterocyclic ring optionally substituted by 1 to 5 Z groups, with the proviso that $R_3$ and $R_4$ may not be simultaneously hydrogen;
X is selected from CO and $SO_2$;
Z is selected from the group consisting of linear or branched alkyl($C_1$-$C_6$), alkenyl($C_2$-$C_6$), alkynyl($C_2$-$C_6$), cycloalkyl($C_3$-$C_6$), haloalkyl($C_2$-$C_6$), hydroxy, —O-alkyl($C_1$-$C_6$), phenoxy, —S-alkyl($C_1$-$C_6$), phenylthio, halogen, nitro, cyano, amino, alkylamino($C_1$-$C_6$) and dialkylamino($C_1$-$C_6$); and pharmaceutically acceptable salts, polymorphs, hydrates, tautomers, solvates and stereoisomers thereof.

Preferably $R_1$ is selected from methyl, chlorine, methoxy, ethoxy, phenylthio or 1-pyrrolidinyl group and $R_2$ is a phenyl group or a phenyl group substituted in para-position by methyl, halogen, methoxy, nitro or trifluoromethyl.

Preferably, X is CO; $R_3$ is selected from the group consisting of hydrogen, linear alkyl($C_1$-$C_6$), phenyl optionally substituted by 1 to 5 Z groups, heteroaryl optionally substituted by 1 to 5 Z groups, amino, —NH-alkyl($C_1$-$C_6$), —N-dialkyl($C_1$-$C_6$), 1-pyrrolidinyl, 4-morpholinyl and 1-piperidinyl; and $R_4$ is selected from the group consisting of hydrogen, linear alkyl($C_1$-$C_6$), phenyl optionally substituted by 1 to 5 Z groups and heteroaryl optionally substituted by 1 to 5 Z groups; or both $R_3$ and $R_4$ can form, together with the nitrogen atom to which they are attached, a 5-6 membered heterocyclic ring optionally substituted by 1 to 5 Z groups; and Z is selected from the group consisting of methyl and methoxy.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids and the like.

Preferred compounds of formula (I) include:
2-(6-Chloro-2-p-tolyl-imidazo[1,2-b]pyridazin-3-yl)-N,N-diethyl-acetamide;
2-(6-Chloro-2-p-tolyl-imidazo[1,2-b]pyridazin-3-yl)-N,N-dipropyl-acetamide;
N,N-Dibutyl-2-(6-chloro-2-p-tolyl-imidazo[1,2-b]pyridazin-3-yl)-acetamide;
2-(6-Chloro-2-p-tolyl-imidazo[1,2-b]pyridazin-3-yl)-1-piperidin-1-yl-ethanone;
2-(6-Chloro-2-p-tolyl-imidazo[1,2-b]pyridazin-3-yl)-1-morpholin-4-yl-ethanone;
2-(6-Chloro-2-p-tolyl-imidazo[1,2-b]pyridazin-3-yl)-1-pyrrolidin-1-yl-ethanone;
N,N-Diethyl-2-(6-pyrrolidin-1-yl-2-p-tolyl-imidazo[1,2-b]pyridazin-3-yl)-acetamide;
N,N-Diethyl-2-(6-methoxy-2-p-tolyl-imidazo[1,2-b]pyridazin-3-yl)-acetamide;
2-[2-(4-Bromo-phenyl)-6-ethoxy-imidazo[1,2-b]pyridazin-3-yl]-1-morpholin-4-yl-ethanone;
2-[2-(4-Bromo-phenyl)-6-ethoxy-imidazo[1,2-b]pyridazin-3-yl]-1-piperidin-1-yl-ethanone;
2-[2-(4-Bromo-phenyl)-6-ethoxy-imidazo[1,2-b]pyridazin-3-yl]-N,N-dibutyl-acetamide;
2-[2-(4-Bromo-phenyl)-6-ethoxy-imidazo[1,2-b]pyridazin-3-yl]-N,N-dipropyl-acetamide;
2-[2-(4-Bromo-phenyl)-6-ethoxy-imidazo[1,2-b]pyridazin-3-yl]-N,N-diethyl-acetamide;
2-[2-(4-Bromo-phenyl)-6-methyl-imidazo[1,2-b]pyridazin-3-yl]-1-morpholin-4-yl-ethanone;
2-[2-(4-Bromo-phenyl)-6-methyl-imidazo[1,2-b]pyridazin-3-yl]-1-piperidin-1-yl-ethanone;
2-[2-(4-Bromo-phenyl)-6-methyl-imidazo[1,2-b]pyridazin-3-yl]-N,N-dibutyl-acetamide;
2-[2-(4-Bromo-phenyl)-6-methyl-imidazo[1,2-b]pyridazin-3-yl]-N,N-dipropyl-acetamide;

2-[2-(4-Bromo-phenyl)-6-methyl-imidazo[1,2-b]pyridazin-3-yl]-N,N-diethyl-acetamide;
2-[2-(4-Chloro-phenyl)-6-methyl-imidazo[1,2-b]pyridazin-3-yl]-N,N-diethyl-acetamide;
2-[2-(4-Chloro-phenyl)-6-ethoxy-imidazo[1,2-b]pyridazin-3-yl]-N,N-diethyl-acetamide;
2-[2-(4-Chloro-phenyl)-6-methyl-imidazo[1,2-b]pyridazin-3-yl]-N,N-dipropyl-acetamide;
N,N-Dibutyl-2-[2-(4-chloro-phenyl)-6-methyl-imidazo[1,2-b]pyridazin-3-yl]-acetamide;
2-[2-(4-Chloro-phenyl)-6-ethoxy-imidazo[1,2-b]pyridazin-3-yl]-N,N-dipropyl-acetamide;
N,N-Dibutyl-2-[2-(4-chloro-phenyl)-6-ethoxy-imidazo[1,2-b]pyridazin-3-yl]-acetamide;
N,N-Diethyl-2-(6-methoxy-2-phenyl-imidazo[1,2-b]pyridazin-3-yl)-acetamide,
2-(6-Methoxy-2-phenyl-imidazo[1,2-b]pyridazin-3-yl)-N,N-dipropyl-acetamide;
N,N-Dibutyl-2-(6-methoxy-2-phenyl-imidazo[1,2-b]pyridazin-3-yl)-acetamide;
2-(6-Methoxy-2-phenyl-imidazo[1,2-b]pyridazin-3-yl)-1-morpholin-4-yl-ethanone;
2-(6-Ethoxy-2-phenyl-imidazo[1,2-b]pyridazin-3-yl)-N,N-diethyl-acetamide;
2-(6-Ethoxy-2-phenyl-imidazo[1,2-b]pyridazin-3-yl)-N,N-dipropyl-acetamide;
N,N-Dibutyl-2-(6-ethoxy-2-phenyl-imidazo[1,2-b]pyridazin-3-yl)-acetamide;
2-(6-Ethoxy-2-phenyl-imidazo[1,2-b]pyridazin-3-yl)-1-morpholin-4-yl-ethanone;
2-(6-Ethoxy-2-phenyl-imidazo[1,2-b]pyridazin-3-yl)-1-piperidin-1-yl-ethanone;
N,N-Diethyl-2-(6-methyl-2-phenyl-imidazo[1,2-b]pyridazin-3-yl)-acetamide;
2-(6-Methyl-2-phenyl-imidazo[1,2-b]pyridazin-3-yl)-N,N-dipropyl-acetamide;
N,N-Dibutyl-2-(6-methyl-2-phenyl-imidazo[1,2-b]pyridazin-3-yl)-acetamide;
2-(6-Methyl-2-phenyl-imidazo[1,2-b]pyridazin-3-yl)-1-morpholin-4-yl-ethanone;
2-(6-Methyl-2-phenyl-imidazo[1,2-b]pyridazin-3-yl)-1-piperidin-1-yl-ethanone;
2-[2-(4-Fluoro-phenyl)-6-methyl-imidazo[1,2-b]pyridazin-3-yl]-N,N-dipropyl-acetamide;
N,N-Dibutyl-2-[2-(4-fluoro-phenyl)-6-methyl-imidazo[1,2-b]pyridazin-3-yl]-acetamide;
2-[2-(4-Fluoro-phenyl)-6-methoxy-imidazo[1,2-b]pyridazin-3-yl]-N,N-dipropyl-acetamide;
N,N-Dibutyl-2-[2-(4-fluoro-phenyl)-6-methoxy-imidazo[1,2-b]pyridazin-3-yl]-acetamide;
2-[6-Ethoxy-2-(4-fluoro-phenyl)-imidazo[1,2-b]pyridazin-3-yl]-N,N-dipropyl-acetamide;
N,N-Dibutyl-2-[6-ethoxy-2-(4-fluoro-phenyl)-imidazo[1,2-b]pyridazin-3-yl]-acetamide;
2-[6-Ethoxy-2-(4-fluoro-phenyl)-imidazo[1,2-b]pyridazin-3-yl]-1-morpholin-4-yl-ethanone;
N,N-Diethyl-2-(6-methoxy-2-p-tolyl-imidazo[1,2-b]pyridazin-3-yl)-acetamide;
2-(6-Methoxy-2-p-tolyl-imidazo[1,2-b]pyridazin-3-yl)-N,N-dipropyl-acetamide;
N,N-Dibutyl-2-(6-methoxy-2-p-tolyl-imidazo[1,2-b]pyridazin-3-yl)-acetamide;
2-(6-Methoxy-2-p-tolyl-imidazo[1,2-b]pyridazin-3-yl)-1-piperidin-1-yl-ethanone;
2-(6-Ethoxy-2-p-tolyl-imidazo[1,2-b]pyridazin-3-yl)-N,N-diethyl-acetamide;
2-(6-Ethoxy-2-p-tolyl-imidazo[1,2-b]pyridazin-3-yl)-N,N-dipropyl-acetamide;
N,N-Dibutyl-2-(6-ethoxy-2-p-tolyl-imidazo[1,2-b]pyridazin-3-yl)-acetamide;
2-(6-Ethoxy-2-p-tolyl-imidazo[1,2-b]pyridazin-3-yl)-1-pyrrolidin-1-yl-ethanone;
2-(6-Ethoxy-2-p-tolyl-imidazo[1,2-b]pyridazin-3-yl)-1-morpholin-4-yl-ethanone;
2-(6-Ethoxy-2-p-tolyl-imidazo[1,2-b]pyridazin-3-yl)-1-piperidin-1-yl-ethanone;
N,N-Diethyl-2-(6-methyl-2-p-tolyl-imidazo[1,2-b]pyridazin-3-yl)-acetamide;
2-(6-Methyl-2-p-tolyl-imidazo[1,2-b]pyridazin-3-yl)-N,N-dipropyl-acetamide;
N,N-Dibutyl-2-(6-methyl-2-p-tolyl-imidazo[1,2-b]pyridazin-3-yl)-acetamide;
2-(6-Methyl-2-p-tolyl-imidazo[1,2-b]pyridazin-3-yl)-1-pyrrolidin-1-yl-ethanone;
2-(6-Methyl-2-p-tolyl-imidazo[1,2-b]pyridazin-3-yl)-1-morpholin-4-yl-ethanone;
2-(6-Methyl-2-p-tolyl-imidazo[1,2-b]pyridazin-3-yl)-1-piperidin-1-yl-ethanone;
N,N-Diethyl-2-[2-(4-fluoro-phenyl)-6-methyl-imidazo[1,2-b]pyridazin-3-yl]-acetamide;
2-[2-(4-Fluoro-phenyl)-6-methyl-imidazo[1,2-b]pyridazin-3-yl]-1-piperidin-1-yl-ethanone;
N,N-Diethyl-2-[2-(4-fluoro-phenyl)-6-methoxy-imidazo[1,2-b]pyridazin-3-yl]-acetamide;
2-[2-(4-Fluoro-phenyl)-6-methoxy-imidazo[1,2-b]pyridazin-3-yl]-1-piperidin-1-yl-ethanone;
2-[6-Ethoxy-2-(4-fluoro-phenyl)-imidazo[1,2-b]pyridazin-3-yl]-N,N-diethyl-acetamide;
2-[6-Ethoxy-2-(4-fluoro-phenyl)-imidazo[1,2-b]pyridazin-3-yl]-1-piperidin-1-yl-ethanone;
2-[2-(4-Fluoro-phenyl)-6-methyl-imidazo[1,2-b]pyridazin-3-yl]-1-morpholin-4-yl-ethanone;
2-[2-(4-Fluoro-phenyl)-6-methoxy-imidazo[1,2-b]pyridazin-3-yl]-1-morpholin-4-yl-ethanone;
N,N-Diethyl-2-[2-(4-methoxy-phenyl)-6-methyl-imidazo[1,2-b]pyridazin-3-yl]-acetamide;
2-[2-(4-Methoxy-phenyl)-6-methyl-imidazo[1,2-b]pyridazin-3-yl]-N,N-dipropyl-acetamide;
N,N-Dibutyl-2-[2-(4-methoxy-phenyl)-6-methyl-imidazo[1,2-b]pyridazin-3-yl]-acetamide;
2-[2-(4-Methoxy-phenyl)-6-methyl-imidazo[1,2-b]pyridazin-3-yl]-1-piperidin-1-yl-ethanone;
2-[2-(4-Methoxy-phenyl)-6-methyl-imidazo[1,2-b]pyridazin-3-yl]-1-morpholin-4-yl-ethanone;
N,N-Diethyl-2-[6-methoxy-2-(4-methoxy-phenyl)-imidazo[1,2-b]pyridazin-3-yl]-acetamide;
2-[6-Methoxy-2-(4-methoxy-phenyl)-imidazo[1,2-b]pyridazin-3-yl]-N,N-dipropyl-acetamide;
N,N-Dibutyl-2-[6-methoxy-2-(4-methoxy-phenyl)-imidazo[1,2-b]pyridazin-3-yl]-acetamide;
2-[6-Methoxy-2-(4-methoxy-phenyl)-imidazo[1,2-b]pyridazin-3-yl]-1-piperidin-1-yl-ethanone;
2-[6-Methoxy-2-(4-methoxy-phenyl)-imidazo[1,2-b]pyridazin-3-yl]-1-morpholin-4-yl-ethanone;
Acetic acid 2-{[2-(6-methyl-2-p-tolyl-imidazo[1,2-b]pyridazin-3-yl)-acetyl]-propyl-amino}-ethyl ester;
1-(3,5-Dimethyl-piperidin-1-yl)-2-(6-methyl-2-p-tolyl-imidazo[1,2-b]pyridazin-3-yl)-ethanone;
N-Cyclopropylmethyl-2-(6-methyl-2-p-tolyl-imidazo[1,2-b]pyridazin-3-yl)-N-propyl-acetamide;
2-(6-Methyl-2-p-tolyl-imidazo[1,2-b]pyridazin-3-yl)-N-thiazol-2-yl-acetamide;

N,N-Diisopropyl-2-(6-methyl-2-p-tolyl-imidazo[1,2-b]pyridazin-3-yl)-acetamide;
N-Cyclohexyl-2-(6-methyl-2-p-tolyl-imidazo[1,2-b]pyridazin-3-yl)-acetamide;
2-(6-Methyl-2-p-tolyl-imidazo[1,2-b]pyridazin-3-yl)-N-phenyl-acetamide;
2-(6-Methyl-2-p-tolyl-imidazo[1,2-b]pyridazin-3-yl)-N-p-tolyl-acetamide;
2-(6-Methyl-2-p-tolyl-imidazo[1,2-b]pyridazin-3-yl)-N-pyridin-2-yl-acetamide;
2-(6-Methyl-2-p-tolyl-imidazo[1,2-b]pyridazin-3-yl)-N-pyridin-2-ylmethyl-acetamide;
N-(3,5-Dimethyl-isoxazol-4-yl)-2-(6-methyl-2-p-tolyl-imidazo[1,2-b]pyridazin-3-yl)-acetamide;
N-Cyclopentyl-2-(6-methyl-2-p-tolyl-imidazo[1,2-b]pyridazin-3-yl)-acetamide,
N,N-Diallyl-2-(6-methyl-2-p-tolyl-imidazo[1,2-b]pyridazin-3-yl)-acetamide;
N-Cyclopropyl-2-(6-methyl-2-p-tolyl-imidazo[1,2-b]pyridazin-3-yl)-acetamide;
2-(6-Methyl-2-p-tolyl-imidazo[1,2-b]pyridazin-3-yl)-N-quinolin-2-yl-acetamide;
N-(5-Methyl-isoxazol-3-yl)-2-(6-methyl-2-p-tolyl-imidazo[1,2-b]pyridazin-3-yl)-acetamide;
N-(4-Methoxy-phenyl)-2-(6-methyl-2-p-tolyl-imidazo[1,2-b]pyridazin-3-yl)-acetamide;
N-(3-Methyl-isoxazol-5-yl)-2-(6-methyl-2-p-tolyl-imidazo[1,2-b]pyridazin-3-yl)-acetamide;
2-(6-Methyl-2-p-tolyl-imidazo[1,2-b]pyridazin-3-yl)-N-[1,3,4]thiadiazol-2-yl-acetamide;
[2-(4-Fluoro-phenyl)-6-pyrrolidin-1-yl-imidazo[1,2-b]pyridazin-3-yl]-acetic acid hydrazide;
[2-(4-Bromo-phenyl)-6-methyl-imidazo[1,2-b]pyridazin-3-yl]-acetic acid hydrazide;
[2-(4-Methoxy-phenyl)-6-methyl-imidazo[1,2-b]pyridazin-3-yl]-acetic acid hydrazide;
[2-(4-Chloro-phenyl)-6-methyl-imidazo[1,2-b]pyridazin-3-yl]-acetic acid hydrazide;
[2-(4-Fluoro-phenyl)-6-methyl-imidazo[1,2-b]pyridazin-3-yl]-acetic acid hydrazide;
(6-Methyl-2-phenyl-imidazo[1,2-b]pyridazin-3-yl)acetic acid hydrazide;
2-(6-Methyl-2-p-tolyl-imidazo[1,2-b]pyridazin-3-yl)-N-morpholin-4-yl-acetamide;
2-(6-Methyl-2-p-tolyl-imidazo[1,2-b]pyridazin-3-yl)-N-piperidin-1-yl-acetamide; and
(6-Methyl-2-p-tolyl-imidazo[1,2-b]pyridazin-3-yl)-acetic acid N',N'-dimethyl-hydrazide.

Another aspect of the present invention is to provide a process for preparing compounds of formula (I) as well as an imidazo[1,2-b]pyridazine intermediate of formula (II):

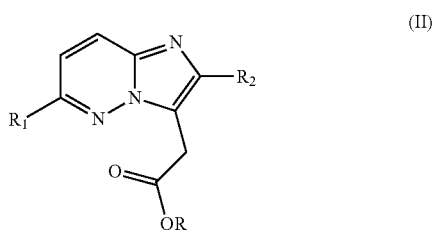

(II)

wherein R is methyl, $R_1$ is a methyl, chlorine, methoxy, ethoxy, thiophenoxy or 1-pyrrolidinyl group and $R_2$ is a phenyl group or a phenyl group substituted in para-position by methyl, halogen, methoxy, nitro or trifluoromethyl.

The compounds of general formula (I), when X is CO, can be obtained following the synthetic strategy showed in Scheme 1.

Scheme 1

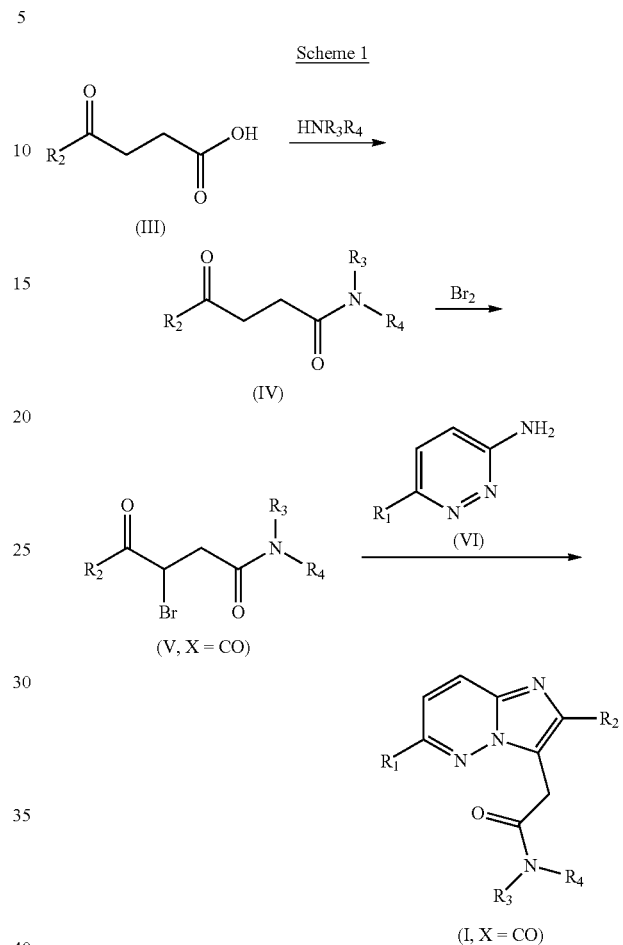

Starting from ketoacids (III), ketoamides (IV) can be obtained by using conventional coupling conditions. These ketoamides (IV) can be brominated in α-position of the reacting carbonyl group with bromine in acetic acid, to yield the bromoketoamides (V). Finally, cyclization of aminopyridazines (VI) in acetonitrile at reflux affords the imidazopyridazines (I, X=CO).

On the other hand, if $R_3$ or $R_4$ are optionally substituted amino groups, then the molecule obtained is not an amide but an hydrazide. The synthetic pathway has to be slightly modified for that proposal (Scheme 2).

Scheme 2

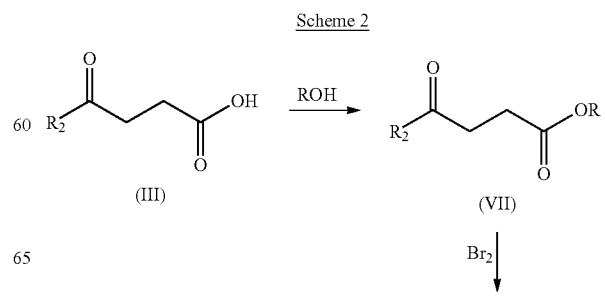

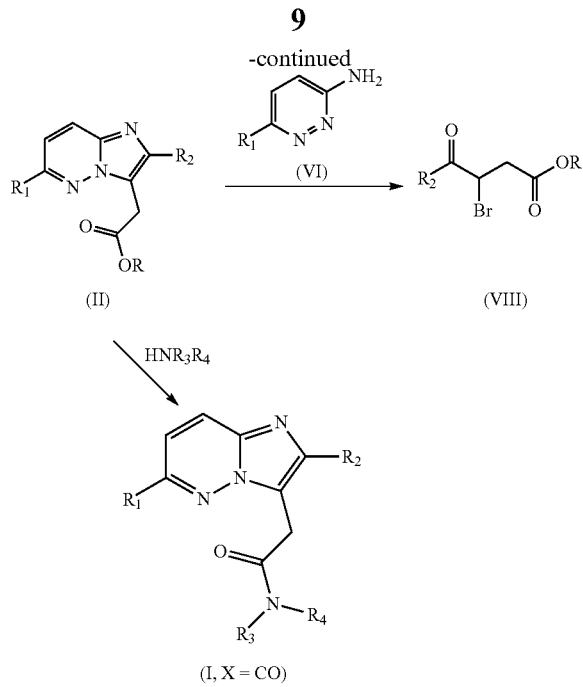

A Fischer esterification of the same ketoacid (III) is carried out with an alcohol ROH to afford the corresponding ester (VII). This ester is brominated under similar conditions as the amide (IV) described above, to yield bromoketoesters (VIII). A cyclization with aminopyridazines (VI) allows the preparation of the imidazopyridazines (II) substituted with an ester group. Finally, acylic substitution by using a substituted hydrazine in a suitable solvent at reflux provides the corresponding hydrazides (I, X=CO, $R_3$ or $R_4$ are optionally substituted amino groups). Suitable solvents to be used in this reaction are selected preferably from linear or branched alkanols ($C_1$-$C_6$), more preferably methanol, or mixtures thereof.

The compounds of the present invention or their pharmaceutically acceptable salts, polymorphs, hydrates, tautomers, solvates and stereoisomers can be used for the preparation of a medicament for treating or preventing diseases associated with $GABA_A$ receptor modulation in a human or non-human mammal. More specifically, diseases associated with $GABA_A$ receptor modulation comprise diseases associated with $\alpha_1$-$GABA_A$ receptor modulation and/or $\alpha_2$-$GABA_A$ receptor modulation. It is well-known for the skill in the art which diseases associated with $GABA_A$ receptor modulation are (cf. Kaufmann W. A. et al., "Compartmentation of alpha 1 and alpha 2 $GABA_A$ receptor subunits within rat extended amygdala: implications for benzodiazepine action", Science 2003, vol. 964 p. 91-99; Möhler H. et al., "$GABA_A$-receptor subtypes: a new pharmacology", Current Opinion in Pharmacology 2001, vol. 1:22-25). A non-limitative list of such diseases comprises anxiety, epilepsy, sleep disorders, including insomnia, and the like.

Another embodiment of the present invention is to provide the use of a compound of formula (I) or a pharmaceutically acceptable salt, polymorph, hydrate, tautomer, solvate and stereoisomer thereof for the preparation of a medicament for treating or preventing anxiety in a human or non-human mammal.

Another embodiment of the present invention is to provide the use of a compound of formula (I) or a pharmaceutically acceptable salt, polymorph, hydrate, tautomer, solvate or stereoisomers thereof for the preparation of a medicament for treating or preventing epilepsy in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for treating or preventing sleep disorders in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for treating or preventing insomnia in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for inducing sedation-hypnosis in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for inducing anesthesia in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for modulating the necessary time to induce sleep and its duration in a human or non-human mammal in need thereof.

Another embodiment of the present invention is to provide the use of a compound of formula (I) or a pharmaceutically acceptable salt, polymorph, hydrate, tautomer, solvate or stereoisomer thereof for the preparation of a medicament for inducing muscle relaxation in a human or non-human mammal in need thereof.

The present invention also relates to a method of treatment or prevention of a human or non-human mammal suffering from diseases associated with $GABA_A$ receptor modulation in a human or non-human mammal, which comprises administering to said human or non-human mammal in need thereof a therapeutically effective amount of a compound of formula (I) or pharmaceutically acceptable salts, polymorphs, hydrates, tautomers, solvates and stereoisomers thereof, together with pharmaceutically acceptable diluents or carriers. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

As used herein, the term "mammal" shall refer to the Mammalian class of higher vertebrates. The term "mammal" includes, but is not limited to, a human.

Another embodiment of the present invention is to provide a pharmaceutical composition containing a compound of formula (I) or pharmaceutically acceptable salts, polymorphs, hydrates, tautomers, solvates and stereoisomers thereof, in association with therapeutically inert carriers.

The compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, micro-crystalline cellulose, diluents, granulating agents, lubricants, binders, disintegrating agents and the like, in the case of oral solid preparations (such as for example, powders, capsules, and tablets) with the oral solid preparations being preferred over the oral liquid preparations.

Because of their ease of administration, tablets and capsules represent the most advantageous oral dosage unit form, in which case solid pharmaceutical carriers are employed. If desired, tablets may be coated by standard aqueous or non-aqueous techniques.

A suitable dosage range for use is from about 0.01 mg to about 100.00 mg total daily dose, given as a once daily administration or in divided doses if required.

The compounds of the present invention have a high affinity for $\alpha_1$ and $\alpha_2$-GABA$_A$ receptors. These in vitro results are consistent with those in vivo results obtained in sedation-hypnosis tests.

In accordance with the results obtained, certain compounds of the present invention have evidenced pharmacological activity both in vitro and in vivo, which has been similar to or higher than that of prior-art compound zolpidem. All these results support their use in diseases or conditions modulated by $\alpha_1$- and $\alpha_2$-GABA$_A$ receptors, such as insomnia or anesthesia, in which an induction of sleep, an induction of sedation or an induction of muscle relaxation are needed.

The pharmacological activity of the compounds of the present invention has been determined as shown below.

a) Ligand-binding Assays. Determination of the Affinity of Test Compounds for $\alpha_1$- and $\alpha_2$-GABA$_A$ Receptor Male Sprague-Dawley rats weighing 200-250 g at the time of experiment were used. After decapitation of the animal, the cerebellum (tissue that mostly contains $\alpha_1$-GABA$_A$ receptor) and spinal cord (tissue that mostly contains $\alpha_2$-GABA$_A$ receptor) were removed. The membranes were prepared according to the method by J. Lameh et al. (Prog. Neuro-Psychopharmacol. Biol. Psychiatry, 24, 979-991, 2000) and H. Noguchi et al. (Eur J Pharm, 434, 21-28, 2002) with slight modifications. Once the tissues weighed, they were suspended in 50 mM Tris.HCl (pH 7.4), 1:40 (v/v), or sucrose 0.32 M in the case of spinal cord, homogenized and then centrifuged at 20000 g for 10 minutes at 7° C. The resulting pellet was resuspended under the same conditions and centrifuged again. The pellet was finally resuspended on a minimum volume and kept at −80° C. overnight. A slight modification was used in the case of spinal cord at the first centrifugation step. Centrifugation speed was at 1000 g and the supernatant was collected instead of discarded as in cerebellum. Then, supernatant was centrifuged at 20000 g and resuspended twice more under the same conditions described above for cerebellum. On the next day, the process was repeated until the final pellet was resuspended at a ratio of 1:10 (v/v) in the case of cerebellum and at a ratio of 1:5 (v/v) in the case of spinal cord.

Affinity was determined by competitive tests using radiolabeled flumazenil as ligand. The tests were performed according to the methods described by S. Arbilla et al. (Eur. J. Pharmacol., 130, 257-263, 1986); and Y. Wu et al. (Eur. J. Pharmacol., 278, 125-132, 1995) using 96-well microtiter plates. The membranes containing the study receptors, flumazenil (radiolabeling at a final concentration of 1 nM) and ascending concentrations of test compounds (in a total volume of 230 µl in 50 mM [pH 7.4] Tris.HCl buffer) were incubated. Simultaneously, the membranes were only incubated with the radiolabeled flumazenil (total binding, 100%) and in the presence of an elevated concentration of unradiolabeled flumazenil (non-specific binding, % estimation of radiolabeled ligand). The reactions started on adding the radiolabeled ligand followed by incubation for 60 minutes at 4° C. At the end of the incubation period, 200 µl of reaction were transferred to a multiscreen plate (Millipore) and filtered using a vacuum manifold and then washed three times with cold test buffer. The multiscreen plates were equipped with a GF/B filter that retained the membranes containing the receptors and the radiolabeled ligand which had been bound to the receptors. After washing, the plates were left till dry. Once dried, scintillation liquid was added and left under stirring overnight. The next day the plates were counted using a Perkin-Elmer Microbeta scintillation counter.

For analysis of the results the percentage of specific binding for every concentration of test compound was calculated as follows:

$$\text{specific binding} = (X - N/T - N) \times 100$$

where,
X: amount of bound ligand for every concentration of compound.
T: total binding, maximum amount bound to the radiolabeled ligand.
N: non-specific binding, amount of radiolabeled ligand bound in a non-specific way irrespective of the receptor used.

Every concentrations of compound were tested in triplicate and their mean values were used to determine the experimental values of % specific binding versus the concentration of compound. Affinity data are expressed as % inhibition at $10^{-5}$ M and $10^{-7}$ M concentrations. The results of these tests are given in Tables 1 and 2.

TABLE 1

Affinity for the $\alpha_1$-subunit of the GABA$_A$ receptor

| Compound | % inhib $10^{-5}$ M | % inhib $10^{-7}$ M |
|---|---|---|
| Example 1 | 100.1 | 98.2 |
| Example 2 | 100.3 | 99.6 |
| Example 3 | 100.2 | 99.4 |
| Example 4 | 99.9 | 98.3 |
| Example 5 | 100.3 | 97.5 |
| Example 6 | 100.0 | 97.4 |
| Example 9 | 96.8 | 11.4 |
| Example 10 | 99.1 | 39.3 |
| Example 11 | 96.0 | 22.0 |
| Example 12 | 96.9 | 34.6 |
| Example 13 | 99.7 | 58.3 |
| Example 14 | 99.5 | 80.6 |
| Example 17 | 99.5 | 97.1 |
| Example 20 | 99.6 | 73.7 |
| Example 22 | 100.0 | 97.6 |
| Example 23 | 99.1 | 61.7 |
| Example 24 | 98.4 | 57.7 |

TABLE 1-continued

Affinity for the $\alpha_1$-subunit of the $GABA_A$ receptor

| Compound | % inhib $10^{-5}$ M | % inhib $10^{-7}$ M |
|---|---|---|
| Example 26 | 100.0 | 73.5 |
| Example 35 | 100.2 | 97.5 |
| Example 40 | 100.3 | 98.0 |
| Example 41 | 99.8 | 75.4 |
| Example 42 | 99.7 | 62.2 |
| Example 43 | 99.5 | 49.9 |
| Example 65 | 99.5 | 58.5 |
| Example 66 | 98.3 | 50.4 |
| Example 67 | 98.9 | 42.2 |
| Example 70 | 99.9 | 84.5 |
| Example 71 | 100.2 | 95.0 |
| Example 72 | 100.4 | 91.5 |
| Example 73 | 99.9 | 76.5 |
| Example 75 | 99.4 | 52.1 |
| Example 77 | 100.1 | 42.2 |
| Example 78 | 98.3 | 26.5 |
| Example 80 | 99.7 | 85.2 |
| Example 81 | 100.1 | 98.5 |
| Example 82 | 100.1 | 99.2 |
| Example 83 | 99.6 | 97.6 |
| Example 84 | 100.0 | 91.7 |
| Example 86 | 99.5 | 75.9 |
| Example 87 | 99.3 | 57.2 |
| Example 88 | 100.2 | 83.9 |
| Example 91 | 99.1 | 45.8 |
| Example 93 | 100.0 | 78.2 |
| Example 94 | 100.1 | 65.1 |
| Example 100 | 99.5 | 62.4 |
| Example 102 | 99.1 | 66.7 |
| Example 105 | 98.8 | 56.0 |
| Example 106 | 99.5 | 53.7 |
| zolpidem | 99.4 | 73.6 |

TABLE 2

Affinity for the $\alpha_2$-subunit of the $GABA_A$ receptor

| Compound | % inhib $10^{-5}$ M | % inhib $10^{-7}$ M |
|---|---|---|
| Example 1 | 94.3 | 49.0 |
| Example 2 | 98.6 | 66.1 |
| Example 3 | 91.3 | 60.8 |
| Example 4 | 97.6 | 53.2 |
| Example 5 | 97.7 | 45.0 |
| Example 6 | 97.5 | 49.4 |
| Example 9 | 61.7 | 5.9 |
| Example 10 | 72.0 | 19.1 |
| Example 11 | 47.0 | 1.7 |
| Example 12 | 71.9 | 2.2 |
| Example 13 | 76.7 | 15.5 |
| Example 14 | 76.9 | 10.8 |
| Example 17 | 83.0 | 36.8 |
| Example 20 | 82.0 | 20.8 |
| Example 22 | 86.6 | 61.2 |
| Example 23 | 80.0 | 0.0 |
| Example 24 | 77.4 | 13.6 |
| Example 26 | 84.5 | 27.4 |
| Example 35 | 92.5 | 57.9 |
| Example 40 | 91.5 | 60.7 |
| Example 41 | 85.3 | 17.0 |
| Example 42 | 79.4 | 16.3 |
| Example 43 | 80.3 | 20.1 |
| Example 65 | 78.5 | 16.3 |
| Example 66 | 79.4 | 7.8 |
| Example 67 | 83.7 | 8.8 |
| Example 70 | 80.3 | 23.6 |
| Example 71 | 88.5 | 50.6 |
| Example 72 | 85.6 | 51.7 |
| Example 73 | 77.0 | 20.6 |
| Example 75 | 68.8 | 9.3 |
| Example 77 | 83.4 | 23.6 |
| Example 80 | 84.3 | 37.0 |
| Example 83 | 93.1 | 57.7 |

TABLE 2-continued

Affinity for the $\alpha_2$-subunit of the $GABA_A$ receptor

| Compound | % inhib $10^{-5}$ M | % inhib $10^{-7}$ M |
|---|---|---|
| Example 84 | 63.9 | 3.1 |
| Example 86 | 80.9 | 23.0 |
| Example 100 | 73.0 | 2.3 |
| Example 102 | 77.9 | 13.7 |
| zolpidem | 74.1 | 19.9 | b) In Vivo Determination of Predictive Sedative-hypnotic Action

The in vivo effects of these compounds were assessed by a predictive sedation-hypnosis test in mice (D. J. Sanger et al., Eur. J. Pharmacol., 313, 35-42, 1996; and G. Griebel et al., Psychopharmacology, 146, 205-213, 1999).

Groups of 5-8 male CD1 mice, weighing 22-26 g at the time of test, were used. The test compounds were administered at 98.0 µmol/kg by mean of intraperitoneal injection. Compounds were suspended in 0.25% agar with one drop of Tween in a volume of 10 mL/kg. Control animals were given the vehicle alone. Using a Smart System (Panlab, S. L., Spain) the traveled distance in cm is recorded for each mouse at 5-minutes intervals during a period of 30 minutes after dosing. The inhibition percentage of traveled distance of treated animals versus control animals (the first 5 minutes were discarded) was calculated. Some compounds were also tested in a lower dose—0.98 µmol/kg—to further discriminate the potency of sedation induction. The results of this test are given in Table 3 and Table 4.

TABLE 3

Determination of in vivo sedative-hypnotic activity in mice at 98.0 µmol/kg

| Compound | % inhib motor activity |
|---|---|
| Example 1 | 94.66 |
| Example 2 | 96.71 |
| Example 3 | 90.94 |
| Example 4 | 94.65 |
| Example 5 | 93.65 |
| Example 6 | 96.86 |
| Example 9 | 93.85 |
| Example 10 | 93.47 |
| Example 11 | 79.82 |
| Example 12 | 83.44 |
| Example 13 | 92.08 |
| Example 14 | 95.56 |
| Example 17 | 93.08 |
| Example 20 | 91.51 |
| Example 22 | 87.97 |
| Example 23 | 91.74 |
| Example 24 | 86.54 |
| Example 26 | 91.55 |
| Example 35 | 80.60 |
| Example 40 | 91.79 |
| Example 41 | 91.18 |
| Example 42 | 91.01 |
| Example 43 | 95.72 |
| Example 65 | 95.46 |
| Example 66 | 95.95 |
| Example 67 | 90.81 |
| Example 70 | 86.98 |
| Example 71 | 95.96 |
| Example 72 | 93.35 |
| Example 73 | 94.07 |
| Example 75 | 92.56 |
| Example 77 | 89.35 |
| Example 78 | 91.14 |
| Example 80 | 94.41 |
| Example 81 | 90.83 |

TABLE 3-continued

Determination of in vivo sedative-hypnotic activity in mice at 98.0 μmol/kg

| Compound | % inhib motor activity |
|---|---|
| Example 82 | 94.22 |
| Example 83 | 88.93 |
| Example 84 | 90.78 |
| Example 86 | 92.62 |
| Example 87 | 90.70 |
| Example 88 | 88.51 |
| Example 91 | 93.05 |
| Example 93 | 93.20 |
| Example 94 | 93.49 |
| Example 100 | 93.71 |
| Example 102 | 85.50 |
| Example 105 | 94.02 |
| Example 106 | 94.05 |
| zolpidem | 91.70 |

TABLE 4

Determination of in vivo sedative-hypnotic activity in mice at 0.98 μmol/kg

| Compound | % inhib motor activity |
|---|---|
| Example 1 | 27.56 |
| Example 2 | 38.39 |
| Example 3 | 14.61 |
| Example 4 | 38.38 |
| Example 5 | 41.15 |
| Example 6 | 51.90 |
| Example 9 | 19.94 |
| Example 10 | 29.54 |
| Example 11 | 15.29 |
| Example 12 | 15.05 |
| Example 13 | 15.11 |
| Example 14 | 4.77 |
| Example 17 | 9.91 |
| Example 22 | 22.21 |
| Example 23 | 12.37 |
| Example 24 | 3.65 |
| Example 26 | 19.19 |
| Example 35 | 6.76 |
| Example 41 | 15.73 |
| zolpidem | 18.30 | c) In Vivo Determination of Predictive Anesthetic Activity

The in vivo effects of these compounds were assessed by a predictive anesthetic test in mice as the loss of righting reflex (Kralic et al., Neuropharmacology, 43(4), 685-689 2002; Belelli et al., Neuropharmacology, 45, 57-71, 2003).

Groups of 5-8 male CD1 mice, weighing 22-26 g at the time of test, were used. The test compounds were administered at 98.0 μmol/kg by mean of intraperitoneal injection. Compounds were suspended in 0.25% agar with one drop of Tween in a volume of 10 mL/kg. Percentage of treated mice which showed loss of righting reflex was calculated.

Interestingly, compounds of examples 2, 3, and 82 exhibited a 90%, 100% and 30% of animals with loss of righting reflex respectively. On the contrary, zolpidem, the prior art compound, exhibited lower anesthetic potential, being necessary to administer double dose than compounds of the present invention to achieve 80% of animals with loss of righting reflex.

d) Comparative Assay

In order to show that the compounds of the present invention are better than other known in the state of the art, particularly those described in the PCT application WO 89/01333, the $IC_{50}$ value for compounds 22, 26, 88, 95, 96, 97 and 98 were calculated and compared to the structurally closest compounds described in said PCT application, i.e., compounds 317 and 318. All these compounds have in common that at 3-position, the imidazo[1,2-b]pyradizine ring have an acetamide. The rest of compounds disclosed in WO89/01333 are not structurally so related with the compounds of the present invention.

The $IC_{50}$ values were estimated from Cheng-Prusoff equation (Cheng Y. C. and Prusoff W. H.; Biochem. Pharmacol. 22, 3099-3108, 1973)

$$Ki = \frac{IC_{50}}{1 + \frac{[RL*]}{Kd}}$$

where,

Ki is determined for each one of the compounds of the invention as described above (section (a)).

[RL*]: radiolabeled ligand concentration (1 nM).

Kd: affinity constant (cerebellum 1.34 nM/spinal cord 1.19 nM)

Table 5 shows the $IC_{50}$ values obtained for the compounds of the present invention and includes the $IC_{50}$ values for compounds 317 and 318 of the PCT application WO89/01333:

TABLE 5

Comparison of $IC_{50}$ values

| Example number | $IC_{50}$ (nM) |
|---|---|
| COMPOUNDS OF THE INVENTION | |
| 22 | 17.2 |
| 88 | 13 |
| 95 | 17.1 |
| 97 | 14.6 |
| 98 | 12.2 |
| COMPOUNDS OF WO89/01333 | |
| 317 | 55 |
| 318 | 474 |

As it is derived from the results obtained, the compounds of the present invention have $IC_{50}$ values lower than the $IC_{50}$ values of WO89/01333, which means that a lower dose of the compounds of the present invention are needed in order to achieve the same therapeutic effect.

The following non-limiting examples illustrate the scope of the present invention.

Example A

General Method for the Preparation of Amides (IV)

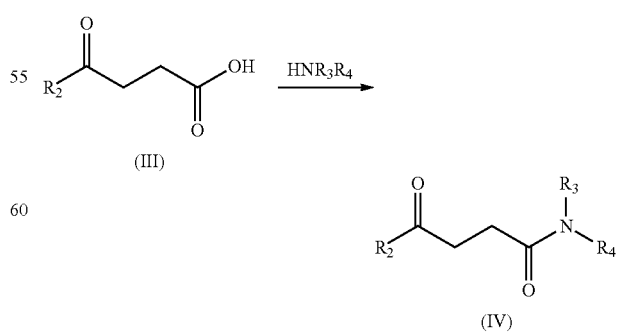

To a solution of the acid (III) (1 eq) in dichloromethane was added a solution of water-soluble carbodiimide (1.5 eq) in dichloromethane. The mixture was stirred at room temperature for 30 minutes. After this period, a solution of 0.5 eq of 4-dimethylamino-pyridine and 1.5 eq of the corresponding amine in dichloromethane was added, and the mixture was stirred for 6 h. The crude was washed with HCl 1 N, the organic layer was dried over $Na_2SO_4$ and filtered off, and the solvent was removed in vacuo, to afford the ketoamide (IV).

E.g. for

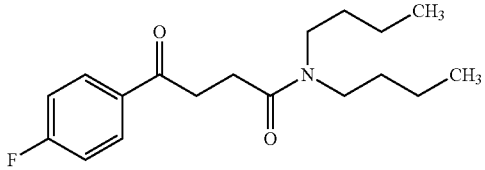 [SMILES: CCCCN(CCCC)C(=O)CCC(=O)c1ccc(F)cc1]

$^1$H NMR (400 MHz, DMSO-$d_6$): δ 7.80-7.15 (m, 4H, Ar), 3.30 (t, 4H, $CH_2N$), 2.87 (t, 2H, $CH_2CO$), 2.47 (t, 2H, $H_2CON$), 1.58-0.93 (m, 14H, $CH_2CH_2CH_3$).

MS (ES) m/z=308 (MH$^+$)

HPLC=100%

Yield=80%

Example B

General Method for the Preparation of Bromoamides (V, X=CO)

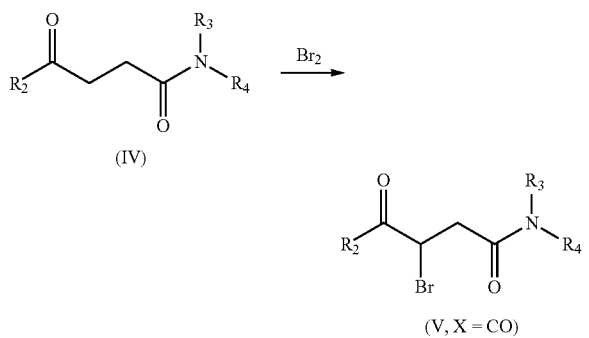

To a solution of (IV) (1 eq) in acetic acid was added dropwise a solution of bromine (2.2 eq) in acetic acid. The mixture was stirred at room temperature for 24 h. The solvent was removed in vacuo and the residue was extracted with dichloromethane/NaOH 1 N and with dichloromethane/water. The organic layer was dried over $Na_2SO_4$ and filtered off, and the solvent was removed in vacuo, thus affording the bromoketoamide (V).

E.g. for

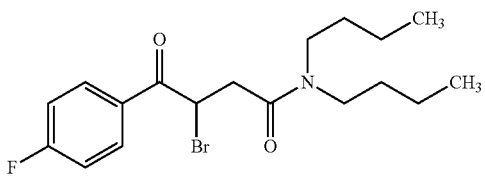 [SMILES: CCCCN(CCCC)C(=O)CC(Br)C(=O)c1ccc(F)cc1]

$^1$H NMR (400 MHz, DMSO-$d_6$): δ 7.97-7.23 (m, 4H, Ar), 5.20 (t, 2H, CHBr), 3.24 (t, 4H, $CH_2N$), 2.87 (d, 2H, $CH_2CON$), 1.75-0.76 (m, 14H, $CH_2CH_2CH_3$).

MS (ES) m/z=380 (M), 382 (M$^+$2H)

HPLC=95%

Yield=34%

Example C

General Method for the Preparation of Imidazopyridazines (I, X=CO)

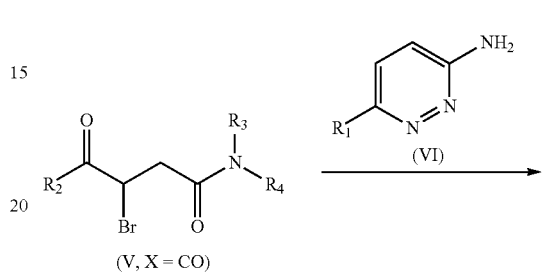

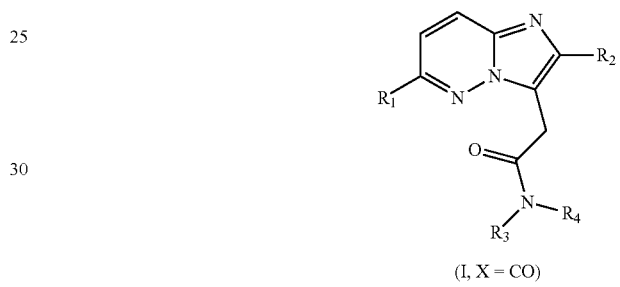

To a solution of (V) (1 eq) in acetonitrile was added a solution of (VI) (1.2 eq) in acetonitrile. The mixture was stirred at reflux for 2 h. The solvent was removed in vacuo and the residue was extracted with dichloromethane/HCl 1 N and with DCM/water. The organic layer was dried over $Na_2SO_4$ and filtered off, and the solvent was removed in vacuo, thus affording the imidazopyridazine (I).

E.g. for

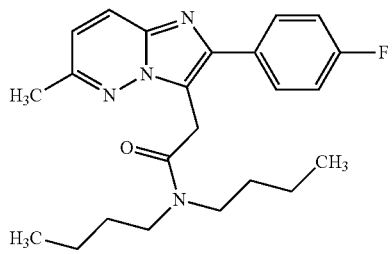 [SMILES: CCCCN(CCCC)C(=O)Cc1c(-c2ccc(F)cc2)nc2ccc(C)nn12]

$^1$H NMR (400 MHz, DMSO-$d_6$): δ 7.30-7.03 (m, 6H, Ar), 3.48 (s, 2H, $CH_2$), 2.32 (s, 3H, $CH_3$), 3.21-0.96 (m, 18H, $CH_2CH_2CH_2CH_3$).

MS (ES) m/z=397 (MH$^+$)

HPLC=89%

Yield=60%

Compounds 1-98 were prepared following this methodology.

| Example Number | MH+ (LCMS) | Purity (UV) | IUPAC NAME |
|---|---|---|---|
| 1 | 358 | 99 | 2-(6-Chloro-2-p-tolyl-imidazo[1,2-b]pyridazin-3-yl)-N,N-diethyl-acetamide |
| 2 | 386 | 99 | 2-(6-Chloro-2-p-tolyl-imidazo[1,2-b]pyridazin-3-yl)-N,N-dipropyl-acetamide |
| 3 | 414 | 97 | N,N-Dibutyl-2-(6-chloro-2-p-tolyl-imidazo[1,2-b]pyridazin-3-yl)-acetamide |
| 4 | 370 | 94 | 2-(6-Chloro-2-p-tolyl-imidazo[1,2-b]pyridazin-3-yl)-1-piperidin-1-yl-ethanone |
| 5 | 372 | 97 | 2-(6-Chloro-2-p-tolyl-imidazo[1,2-b]pyridazin-3-yl)-1-morpholin-4-yl-ethanone |
| 6 | 356 | 83 | 2-(6-Chloro-2-p-tolyl-imidazo[1,2-b]pyridazin-3-yl)-1-pyrrolidin-1-yl-ethanone |
| 7 | 393 | 100 | N,N-Diethyl-2-(6-pyrrolidin-1-yl-2-p-tolyl-imidazo[1,2-b]pyridazin-3-yl)-acetamide |
| 8 | 353 | 84 | N,N-Diethyl-2-(6-methoxy-2-p-tolyl-imidazo[1,2-b]pyridazin-3-yl)-acetamide |
| 9 | 446 | 84 | 2-[2-(4-Bromo-phenyl)-6-ethoxy-imidazo[1,2-b]pyridazin-3-yl]-1-morpholin-4-yl-ethanone |
| 10 | 444 | 100 | 2-[2-(4-Bromo-phenyl)-6-ethoxy-imidazo[1,2-b]pyridazin-3-yl]-1-piperidin-1-yl-ethanone |
| 11 | 488 | 100 | 2-[2-(4-Bromo-phenyl)-6-ethoxy-imidazo[1,2-b]pyridazin-3-yl]-N,N-dibutyl-acetamide |
| 12 | 460 | 100 | 2-[2-(4-Bromo-phenyl)-6-ethoxy-imidazo[1,2-b]pyridazin-3-yl]-N,N-dipropyl-acetamide |
| 13 | 432 | 80 | 2-[2-(4-Bromo-phenyl)-6-ethoxy-imidazo[1,2-b]pyridazin-3-yl]-N,N-diethyl-acetamide |
| 14 | 416 | 86 | 2-[2-(4-Bromo-phenyl)-6-methyl-imidazo[1,2-b]pyridazin-3-yl]-1-morpholin-4-yl-ethanone |
| 15 | 414 | 96 | 2-[2-(4-Bromo-phenyl)-6-methyl-imidazo[1,2-b]pyridazin-3-yl]-1-piperidin-1-yl-ethanone |
| 16 | 458 | 99 | 2-[2-(4-Bromo-phenyl)-6-methyl-imidazo[1,2-b]pyridazin-3-yl]-N,N-dibutyl-acetamide |
| 17 | 430 | 99 | 2-[2-(4-Bromo-phenyl)-6-methyl-imidazo[1,2-b]pyridazin-3-yl]-N,N-dipropyl-acetamide |
| 18 | 402 | 98 | 2-[2-(4-Bromo-phenyl)-6-methyl-imidazo[1,2-b]pyridazin-3-yl]-N,N-diethyl-acetamide |
| 19 | 358 | 94 | 2-[2-(4-Chloro-phenyl)-6-methyl-imidazo[1,2-b]pyridazin-3-yl]-N,N-diethyl-acetamide |
| 20 | 388 | 87 | 2-[2-(4-Chloro-phenyl)-6-ethoxy-imidazo[1,2-b]pyridazin-3-yl]-N,N-diethyl-acetamide |
| 21 | 386 | 100 | 2-[2-(4-Chloro-phenyl)-6-methyl-imidazo[1,2-b]pyridazin-3-yl]-N,N-dipropyl-acetamide |
| 22 | 414 | 99 | N,N-Dibutyl-2-[2-(4-chloro-phenyl)-6-methyl-imidazo[1,2-b]pyridazin-3-yl]-acetamide |
| 23 | 416 | 98 | 2-[2-(4-Chloro-phenyl)-6-ethoxy-imidazo[1,2-b]pyridazin-3-yl]-N,N-dipropyl-acetamide |
| 24 | 444 | 100 | N,N-Dibutyl-2-[2-(4-chloro-phenyl)-6-ethoxy-imidazo[1,2-b]pyridazin-3-yl]-acetamide |
| 25 | 339 | 80 | N,N-Diethyl-2-(6-methoxy-2-phenyl-imidazo[1,2-b]pyridazin-3-yl)-acetamide |
| 26 | 367 | 96 | 2-(6-Methoxy-2-phenyl-imidazo[1,2-b]pyridazin-3-yl)-N,N-dipropyl-acetamide |
| 27 | 396 | 87 | N,N-Dibutyl-2-(6-methoxy-2-phenyl-imidazo[1,2-b]pyridazin-3-yl)-acetamide |
| 28 | 353 | 100 | 2-(6-Methoxy-2-phenyl-imidazo[1,2-b]pyridazin-3-yl)-1-morpholin-4-yl-ethanone |
| 29 | 353 | 83 | 2-(6-Ethoxy-2-phenyl-imidazo[1,2-b]pyridazin-3-yl)-N,N-diethyl-acetamide |
| 30 | 381 | 100 | 2-(6-Ethoxy-2-phenyl-imidazo[1,2-b]pyridazin-3-yl)-N,N-dipropyl-acetamide |
| 31 | 410 | 100 | N,N-Dibutyl-2-(6-ethoxy-2-phenyl-imidazo[1,2-b]pyridazin-3-yl)-acetamide |
| 32 | 367 | 88 | 2-(6-Ethoxy-2-phenyl-imidazo[1,2-b]pyridazin-3-yl)-1-morpholin-4-yl-ethanone |
| 33 | 365 | 80 | 2-(6-Ethoxy-2-phenyl-imidazo[1,2-b]pyridazin-3-yl)-1-piperidin-1-yl-ethanone |
| 34 | 323 | 80 | N,N-Diethyl-2-(6-methyl-2-phenyl-imidazo[1,2-b]pyridazin-3-yl)-acetamide |
| 35 | 351 | 100 | 2-(6-Methyl-2-phenyl-imidazo[1,2-b]pyridazin-3-yl)-N,N-dipropyl-acetamide |
| 36 | 380 | 88 | N,N-Dibutyl-2-(6-methyl-2-phenyl-imidazo[1,2-b]pyridazin-3-yl)-acetamide |
| 37 | 337 | 100 | 2-(6-Methyl-2-phenyl-imidazo[1,2-b]pyridazin-3-yl)-1-morpholin-4-yl-ethanone |
| 38 | 335 | 81 | 2-(6-Methyl-2-phenyl-imidazo[1,2-b]pyridazin-3-yl)-1-piperidin-1-yl-ethanone |
| 39 | 369 | 89 | 2-[2-(4-Fluoro-phenyl)-6-methyl-imidazo[1,2-b]pyridazin-3-yl]-N,N-dipropyl-acetamide |

-continued

| Example Number | MH+ (LCMS) | Purity (UV) | IUPAC NAME |
|---|---|---|---|
| 40 | 398 | 89 | N,N-Dibutyl-2-[2-(4-fluoro-phenyl)-6-methyl-imidazo[1,2-b]pyridazin-3-yl]-acetamide |
| 41 | 385 | 90 | 2-[2-(4-Fluoro-phenyl)-6-methoxy-imidazo[1,2-b]pyridazin-3-yl]-N,N-dipropyl-acetamide |
| 42 | 414 | 92 | N,N-Dibutyl-2-[2-(4-fluoro-phenyl)-6-methoxy-imidazo[1,2-b]pyridazin-3-yl]-acetamide |
| 43 | 399 | 85 | 2-[6-Ethoxy-2-(4-fluoro-phenyl)-imidazo[1,2-b]pyridazin-3-yl]-N,N-dipropyl-acetamide |
| 44 | 428 | 93 | N,N-Dibutyl-2-[6-ethoxy-2-(4-fluoro-phenyl)-imidazo[1,2-b]pyridazin-3-yl]-acetamide |
| 45 | 385 | 80 | 2-[6-Ethoxy-2-(4-fluoro-phenyl)-imidazo[1,2-b]pyridazin-3-yl]-1-morpholin-4-yl-ethanone |
| 46 | 353 | 97 | N,N-Diethyl-2-(6-methoxy-2-p-tolyl-imidazo[1,2-b]pyridazin-3-yl)-acetamide |
| 47 | 381 | 82 | 2-(6-Methoxy-2-p-tolyl-imidazo[1,2-b]pyridazin-3-yl)-N,N-dipropyl-acetamide |
| 48 | 410 | 90 | N,N-Dibutyl-2-(6-methoxy-2-p-tolyl-imidazo[1,2-b]pyridazin-3-yl)-acetamide |
| 49 | 365 | 80 | 2-(6-Methoxy-2-p-tolyl-imidazo[1,2-b]pyridazin-3-yl)-1-piperidin-1-yl-ethanone |
| 50 | 367 | 85 | 2-(6-Ethoxy-2-p-tolyl-imidazo[1,2-b]pyridazin-3-yl)-N,N-diethyl-acetamide |
| 51 | 396 | 80 | 2-(6-Ethoxy-2-p-tolyl-imidazo[1,2-b]pyridazin-3-yl)-N,N-dipropyl-acetamide |
| 52 | 424 | 89 | N,N-Dibutyl-2-(6-ethoxy-2-p-tolyl-imidazo[1,2-b]pyridazin-3-yl)-acetamide |
| 53 | 365 | 81 | 2-(6-Ethoxy-2-p-tolyl-imidazo[1,2-b]pyridazin-3-yl)-1-pyrrolidin-1-yl-ethanone |
| 54 | 381 | 85 | 2-(6-Ethoxy-2-p-tolyl-imidazo[1,2-b]pyridazin-3-yl)-1-morpholin-4-yl-ethanone |
| 55 | 379 | 80 | 2-(6-Ethoxy-2-p-tolyl-imidazo[1,2-b]pyridazin-3-yl)-1-piperidin-1-yl-ethanone |
| 56 | 337 | 90 | N,N-Diethyl-2-(6-methyl-2-p-tolyl-imidazo[1,2-b]pyridazin-3-yl)-acetamide |
| 57 | 365 | 90 | 2-(6-Methyl-2-p-tolyl-imidazo[1,2-b]pyridazin-3-yl)-N,N-dipropyl-acetamide |
| 58 | 394 | 90 | N,N-Dibutyl-2-(6-methyl-2-p-tolyl-imidazo[1,2-b]pyridazin-3-yl)-acetamide |
| 59 | 335 | 80 | 2-(6-Methyl-2-p-tolyl-imidazo[1,2-b]pyridazin-3-yl)-1-pyrrolidin-1-yl-ethanone |
| 60 | 351 | 85 | 2-(6-Methyl-2-p-tolyl-imidazo[1,2-b]pyridazin-3-yl)-1-morpholin-4-yl-ethanone |
| 61 | 349 | 85 | 2-(6-Methyl-2-p-tolyl-imidazo[1,2-b]pyridazin-3-yl)-1-piperidin-1-yl-ethanone |
| 62 | 341 | 87 | N,N-Diethyl-2-[2-(4-fluoro-phenyl)-6-methyl-imidazo[1,2-b]pyridazin-3-yl]-acetamide |
| 63 | 353 | 81 | 2-[2-(4-Fluoro-phenyl)-6-methyl-imidazo[1,2-b]pyridazin-3-yl]-1-piperidin-1-yl-ethanone |
| 64 | 357 | 90 | N,N-Diethyl-2-[2-(4-fluoro-phenyl)-6-methoxy-imidazo[1,2-b]pyridazin-3-yl]-acetamide |
| 65 | 369 | 94 | 2-[2-(4-Fluoro-phenyl)-6-methoxy-imidazo[1,2-b]pyridazin-3-yl]-1-piperidin-1-yl-ethanone |
| 66 | 371 | 91 | 2-[6-Ethoxy-2-(4-fluoro-phenyl)-imidazo[1,2-b]pyridazin-3-yl]-N,N-diethyl-acetamide |
| 67 | 383 | 91 | 2-[6-Ethoxy-2-(4-fluoro-phenyl)-imidazo[1,2-b]pyridazin-3-yl]-1-piperidin-1-yl-ethanone |
| 68 | 355 | 92 | 2-[2-(4-Fluoro-phenyl)-6-methyl-imidazo[1,2-b]pyridazin-3-yl]-1-morpholin-4-yl-ethanone |
| 69 | 371 | 95 | 2-[2-(4-Fluoro-phenyl)-6-methoxy-imidazo[1,2-b]pyridazin-3-yl]-1-morpholin-4-yl-ethanone |
| 70 | 353 | 99 | N,N-Diethyl-2-[2-(4-methoxy-phenyl)-6-methyl-imidazo[1,2-b]pyridazin-3-yl]-acetamide |
| 71 | 381 | 99 | 2-[2-(4-Methoxy-phenyl)-6-methyl-imidazo[1,2-b]pyridazin-3-yl]-N,N-dipropyl-acetamide |
| 72 | 410 | 100 | N,N-Dibutyl-2-[2-(4-methoxy-phenyl)-6-methyl-imidazo[1,2-b]pyridazin-3-yl]-acetamide |
| 73 | 365 | 100 | 2-[2-(4-Methoxy-phenyl)-6-methyl-imidazo[1,2-b]pyridazin-3-yl]-1-piperidin-1-yl-ethanone |
| 74 | 367 | 92 | 2-[2-(4-Methoxy-phenyl)-6-methyl-imidazo[1,2-b]pyridazin-3-yl]-1-morpholin-4-yl-ethanone |
| 75 | 369 | 100 | N,N-Diethyl-2-[6-methoxy-2-(4-methoxy-phenyl)-imidazo[1,2-b]pyridazin-3-yl]-acetamide |
| 76 | 397 | 98 | 2-[6-Methoxy-2-(4-methoxy-phenyl)-imidazo[1,2-b]pyridazin-3-yl]-N,N-dipropyl-acetamide |

| Example Number | MH+ (LCMS) | Purity (UV) | IUPAC NAME |
|---|---|---|---|
| 77 | 426 | 100 | N,N-Dibutyl-2-[6-methoxy-2-(4-methoxy-phenyl)-imidazo[1,2-b]pyridazin-3-yl]-acetamide |
| 78 | 381 | 100 | 2-[6-Methoxy-2-(4-methoxy-phenyl)-imidazo[1,2-b]pyridazin-3-yl]-1-piperidin-1-yl-ethanone |
| 79 | 383 | 97 | 2-[6-Methoxy-2-(4-methoxy-phenyl)-imidazo[1,2-b]pyridazin-3-yl]-1-morpholin-4-yl-ethanone |
| 80 | 410 | 94 | Acetic acid 2-{[2-(6-methyl-2-p-tolyl-imidazo[1,2-b]pyridazin-3-yl)-acetyl]-propyl-amino}-ethyl ester |
| 81 | 378 | 89 | 1-(3,5-Dimethyl-piperidin-1-yl)-2-(6-methyl-2-p-tolyl-imidazo[1,2-b]pyridazin-3-yl)-ethanone |
| 82 | 378 | 93 | N-Cyclopropylmethyl-2-(6-methyl-2-p-tolyl-imidazo[1,2-b]pyridazin-3-yl)-N-propyl-acetamide |
| 83 | 364 | 98 | 2-(6-Methyl-2-p-tolyl-imidazo[1,2-b]pyridazin-3-yl)-N-thiazol-2-yl-acetamide |
| 84 | 365 | 97 | N,N-Diisopropyl-2-(6-methyl-2-p-tolyl-imidazo[1,2-b]pyridazin-3-yl)-acetamide |
| 85 | 363 | 96 | N-Cyclohexyl-2-(6-methyl-2-p-tolyl-imidazo[1,2-b]pyridazin-3-yl)-acetamide |
| 86 | 357 | 95 | 2-(6-Methyl-2-p-tolyl-imidazo[1,2-b]pyridazin-3-yl)-N-phenyl-acetamide |
| 87 | 371 | 99 | 2-(6-Methyl-2-p-tolyl-imidazo[1,2-b]pyridazin-3-yl)-N-p-tolyl-acetamide |
| 88 | 358 | 96 | 2-(6-Methyl-2-p-tolyl-imidazo[1,2-b]pyridazin-3-yl)-N-pyridin-2-yl-acetamide |
| 89 | 372 | 94 | 2-(6-Methyl-2-p-tolyl-imidazo[1,2-b]pyridazin-3-yl)-N-pyridin-2-ylmethyl-acetamide |
| 90 | 376 | 99 | N-(3,5-Dimethyl-isoxazol-4-yl)-2-(6-methyl-2-p-tolyl-imidazo[1,2-b]pyridazin-3-yl)-acetamide |
| 91 | 349 | 93 | N-Cyclopentyl-2-(6-methyl-2-p-tolyl-imidazo[1,2-b]pyridazin-3-yl)-acetamide |
| 92 | 361 | 82 | N,N-Diallyl-2-(6-methyl-2-p-tolyl-imidazo[1,2-b]pyridazin-3-yl)-acetamide |
| 93 | 321 | 97 | N-Cyclopropyl-2-(6-methyl-2-p-tolyl-imidazo[1,2-b]pyridazin-3-yl)-acetamide |
| 94 | 408 | 95 | 2-(6-Methyl-2-p-tolyl-imidazo[1,2-b]pyridazin-3-yl)-N-quinolin-2-yl-acetamide |
| 95 | 362 | 95 | N-(5-Methyl-isoxazol-3-yl)-2-(6-methyl-2-p-tolyl-imidazo[1,2-b]pyridazin-3-yl)-acetamide |
| 96 | 387 | 99 | N-(4-Methoxy-phenyl)-2-(6-methyl-2-p-tolyl-imidazo[1,2-b]pyridazin-3-yl)-acetamide |
| 97 | 362 | 99 | N-(3-Methyl-isoxazol-5-yl)-2-(6-methyl-2-p-tolyl-imidazo[1,2-b]pyridazin-3-yl)-acetamide |
| 98 | 365 | 99 | 2-(6-Methyl-2-p-tolyl-imidazo[1,2-b]pyridazin-3-yl)-N-[1,3,4]thiadiazol-2-yl-acetamide |

Example D

General Method for the Preparation of Ketoesters (VII)

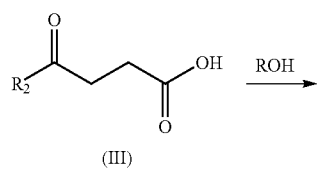

(III)

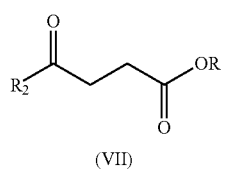

(VII)

To a solution of (III) (1 eq) in methanol (ROH, R=CH$_3$) was added dropwise a solution of concentrated H$_2$SO$_4$ (0.5 eq) in methanol. The mixture was stirred at reflux for 30 minutes. The solvent was removed in vacuo and the residue was extracted with dichloromethane/NaOH 1 N and with dichloromethane/water. The organic layer was dried over Na$_2$SO$_4$ and filtered off, and the solvent was removed in vacuo, thus affording the ketoester (VIII).

E.g. for

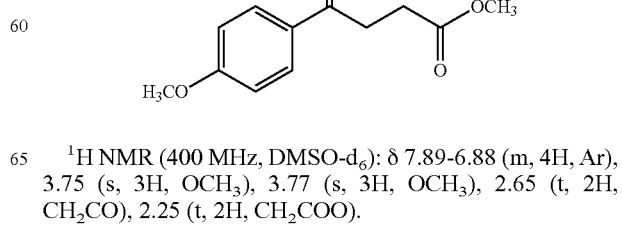

$^1$H NMR (400 MHz, DMSO-d$_6$): δ 7.89-6.88 (m, 4H, Ar), 3.75 (s, 3H, OCH$_3$), 3.77 (s, 3H, OCH$_3$), 2.65 (t, 2H, CH$_2$CO), 2.25 (t, 2H, CH$_2$COO).

MS (ES) m/z=223 (MH$^+$)
HPLC=95%
Yield=93%

Example E

General Method for the Preparation of Bromoketoesters (VIII)

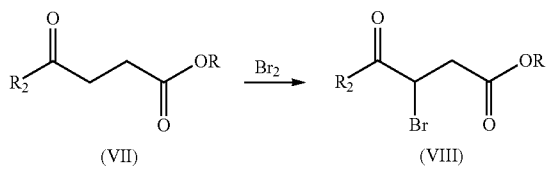

(VII)  (VIII)

To a solution of (VII) (1 eq) in acetic acid was added dropwise a solution of bromine (2.2 eq) in acetic acid. The mixture was stirred at room temperature for 24 h. The solvent was removed in vacuo and the residue was extracted with dichloromethane/NaOH 1 N and with dichloromethane/water. The organic layer was dried over Na$_2$SO$_4$ and filtered off, and the solvent was removed in vacuo, thus affording the bromoketoester (VIII).

E.g. for

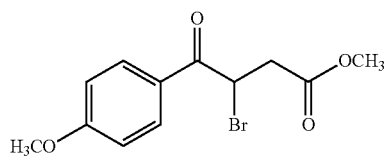 [SMILES: COC(=O)CC(Br)C(=O)c1ccc(OC)cc1]

$^1$H NMR (400 MHz, DMSO-d$_6$): δ 7.98-6.82 (m, 4H, Ar), 5.38 (t, 1H, CHBr), 3.98 (s, 3H, OCH$_3$), 3.54 (s, 3H, OCH$_3$), 2.75 (t, 2H, CH$_2$COO).
MS (ES) m/z=301 (M), 303 (M$^+$2H)
HPLC=95%
Yield=35%

Example F

General Method for the Preparation of Imidazopyridazines (II)

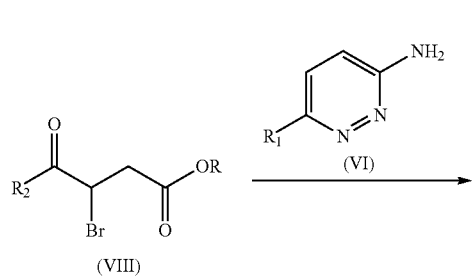

(VIII)

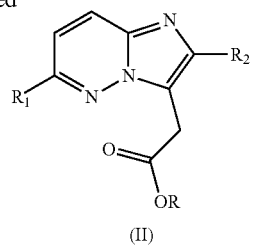

(II)

To a solution of (VIII) (1 eq) in acetonitrile was added a solution of (VI) (1.2 eq) in acetonitrile. The mixture was stirred at reflux for 2 h. The solvent was removed in vacuo and the residue was extracted with dichloromethane/HCl 1 N and with dichloromethane/water. The organic layer was dried over Na$_2$SO$_4$ and filtered off, and the solvent was removed in vacuo, thus affording the imidazopyridazine (II).

E.g. for

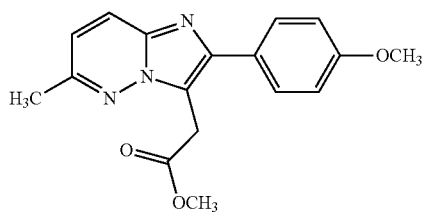 [SMILES: COC(=O)Cc1c(-c2ccc(OC)cc2)nc2ccc(C)nn12]

$^1$H NMR (400 MHz, DMSO-d$_6$): δ 7.69-6.79 (m, 6H, Ar), 3.75 (s, 3H, OCH$_3$), 3.67 (s, 3H, OCH$_3$), 3.35 (s, 2H, CH$_2$), 2.17 (s, 31-1, CH$_3$).
MS (ES) m/z=312 (MH$^+$)
HPLC=90%
Yield=60%

Example G

General Method for the Preparation of Imidazopyridazines (I, X=CO, R$_3$ or R$_4$ are Substitued Amino Groups)

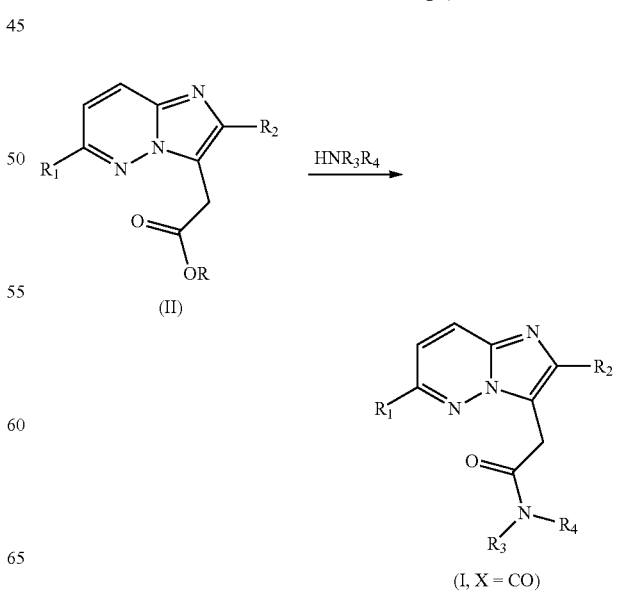

To a solution of (II) (1 eq) in methanol was added a solution of (substituted) hydrazine (5 eq) in methanol. The mixture was stirred at reflux for 24 h. The solvent was removed in vacuo and the residue was extracted with dichloromethane/HCl 1 N and with dichloromethane/water. The organic layer was dried over $Na_2SO_4$ and filtered off, and the solvent was removed in vacuo, thus affording the imidazopyridazine (I).

E.g. for

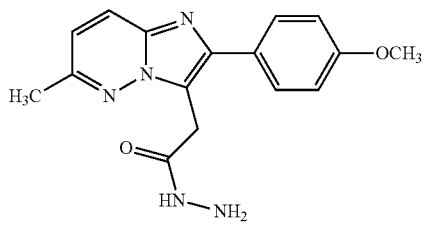 [SMILES: COc1ccc(-c2nc3ccc(C)nn3c2CC(=O)NN)cc1]

$^1$H NMR (400 MHz, DMSO-$d_6$): δ 8.00 (bs, 1H, NH), 7.50-6.93 (m, 6H, Ar), 3.78 (s, 3H, $OCH_3$), 3.96 (s, 3H, $OCH_3$), 3.28 (s, 2H, $CH_2$), 2.12 (bs, 2H, $NH_2$).

MS (ES) m/z=312 (MH$^+$)

HPLC=93%

Yield=65%

Compounds 99-107 were prepared following this methodology.

| Example Number | MH$^+$ (LCMS) | Purity (UV) | IUPAC NAME |
|---|---|---|---|
| 99 | 355 | 100 | [2-(4-Fluoro-phenyl)-6-pyrrolidin-1-yl-imidazo[1,2-b]pyridazin-3-yl]-acetic acid hydrazide |
| 100 | 361 | 100 | [2-(4-Bromo-phenyl)-6-methyl-imidazo[1,2-b]pyridazin-3-yl]-acetic acid hydrazide |
| 101 | 312 | 93 | [2-(4-Methoxy-phenyl)-6-methyl-imidazo[1,2-b]pyridazin-3-yl]-acetic acid hydrazide |
| 102 | 317 | 99 | [2-(4-Chloro-phenyl)-6-methyl-imidazo[1,2-b]pyridazin-3-yl]-acetic acid hydrazide |
| 103 | 300 | 92 | [2-(4-Fluoro-phenyl)-6-methyl-imidazo[1,2-b]pyridazin-3-yl]-acetic acid hydrazide |
| 104 | 282 | 99 | (6-Methyl-2-phenyl-imidazo[1,2-b]pyridazin-3-yl)-acetic acid hydrazide |
| 105 | 366 | 91 | 2-(6-Methyl-2-p-tolyl-imidazo[1,2-b]pyridazin-3-yl)-N-morpholin-4-yl-acetamide |
| 106 | 364 | 90 | 2-(6-Methyl-2-p-tolyl-imidazo[1,2-b]pyridazin-3-yl)-N-piperidin-1-yl-acetamide |
| 107 | 324 | 91 | (6-Methyl-2-p-tolyl-imidazo[1,2-b]pyridazin-3-yl)-acetic acid N',N'-dimethyl-hydrazide |

Composition Example 1

5 mg Tablets

| | |
|---|---|
| Active ingredient | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 2

10 mg Capsules

| | |
|---|---|
| Active ingredient | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

Composition Example 3

Oral Drops

| | |
|---|---|
| Active ingredient | 0.5 g |
| Propylene glycol | 10.0 g |
| Glycerin | 5.0 g |
| Saccharin sodium | 0.1 g |

-continued

| | |
|---|---|
| Polysorbate 80 | 1.0 g |
| Lemon flavor | 0.2 g |
| Ethanol | 25.0 mL |
| Purified water q.s. to | 100.0 mL |

Composition Example 4

2.5 mg Tablets

| | |
|---|---|
| Active ingredient | 2.5 mg |
| Colloidal silicon dioxide | 0.6 mg |
| Croscaramellose sodium | 12.0 mg |
| Talc | 4.0 mg |

-continued

|  |  |
|---|---|
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Composition Example 5

5 mg Capsules

|  |  |
|---|---|
| Active ingredient | 5.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

Composition Example 6

Oral Drops

|  |  |
|---|---|
| Active ingredient | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

The invention claimed is:

1. An imidazo[1,2-b]pyridazine compound of formula (I)

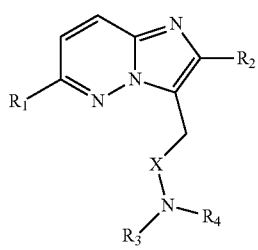

(I)

wherein
R$_1$ is a methyl, chlorine, methoxy, ethoxy, phenylthio or 1-pyrrolidinyl group;
R$_2$ is a phenyl group or a phenyl group substituted in para-position by methyl, halogen, methoxy, nitro or trifluoromethyl;
R$_3$ and R$_4$ are independently selected from the group consisting of linear or branched alkyl(C$_1$-C$_6$), alkenyl (C$_2$-C$_6$), alkynyl(C$_2$-C$_6$), cycloalkyl(C$_3$-C$_6$), hydroxyalkyl(C$_1$-C$_6$), amino, —NH-alkyl(C$_1$-C$_6$), —N-dialkyl(C$_1$-C$_6$), pyrrolidinyl, morpholinyl, piperidinyl, —N-alkyl(C$_1$-C$_6$)piperazinyl, —N-acyl(C$_1$-C$_6$)piperazinyl, phenyl optionally substituted by 1 to 5 Z groups and heteroaryl optionally substituted by 1 to 5 Z groups, or both R$_3$ and R$_4$ can form, together with the nitrogen atom to which they are attached, a 5-6 membered heterocyclic ring optionally substituted by 1 to 5 Z groups;
X is selected from CO and SO$_2$;
Z is selected from the group consisting of linear or branched alkyl(C1-C6), alkenyl(C$_2$-C$_6$), alkynyl(C$_2$-C$_6$), cycloalkyl(C$_3$-C$_6$), haloalkyl(C$_2$-C$_6$), hydroxy, —O-alkyl(C$_1$-C$_6$), phenoxy, —S-alkyl(C$_1$-C$_6$), phenylthio, halogen, nitro, cyano, amino, alkylamino(C$_1$-C$_6$) and dialkylamino (C$_1$-C$_6$);
or
a pharmaceutically acceptable salt, polymorph, hydrate, tautomer, solvate or stereoisomer thereof.

2. The compound according to claim 1, wherein
X is CO;
R$_3$ is selected from the group consisting of linear alkyl(C$_1$-C$_6$), phenyl optionally substituted by 1 to 5 Z groups, heteroaryl optionally substituted by 1 to 5 Z groups, amino, —NH-alkyl(C$_1$-C$_6$), —N-dialkyl(C$_1$-C$_6$), 1-pyrrolidinyl, 4-morpholinyl and 1-piperidinyl; and
R$_4$ is selected from the group consisting of linear alkyl(C$_1$-C$_6$), phenyl optionally substituted by 1 to 5 Z groups and heteroaryl optionally substituted by 1 to 5 Z groups; or
both R$_3$ and R$_4$ can form, together with the nitrogen atom to which they are attached, a 5-6 membered heterocyclic ring optionally substituted by 1 to 5 Z groups; and
Z is selected from the group consisting of methyl and methoxy;
or
a pharmaceutically acceptable salt, polymorph, hydrate, tautomer, solvate or stereoisomers thereof.

3. The compound according to claim 1, wherein said compound is
2-[2-(4-Fluoro-phenyl)-6-methyl-imidazo[1,2-b]pyridazin-3-yl]-1-morpholin-4-yl-ethanone or a pharmaceutically acceptable salt, polymorph, hydrate, tautomer, or solvate thereof.

4. A method for treating or preventing diseases associated with the GABA$_A$ receptor modulation in a human or non-human mammal in need thereof comprising administering a therapeutically effective amount of the compound of claim 1 to the human or non-human mammal.

5. The method of claim 4, wherein the GABA$_A$ receptor is the α$_1$-GABA$_A$ receptor.

6. The method of claim 4, wherein the GABA$_A$ receptor is the α$_2$-GABA$_A$ receptor.

7. A method for treating or preventing anxiety in a human or non-human mammal comprising administering a therapeutically effective amount of the compound of claim 1 to the human or non-human mammal.

8. A method for treating or preventing epilepsy in a human or non-human mammal comprising administering a therapeutically effective amount of the compound of claim 1 to the human or non-human mammal.

9. A method for treating or preventing sleep disorders in a human or non-human mammal comprising administering a therapeutically effective amount of the compound of claim 1 to the human or non-human mammal.

10. A method for treating or preventing insomnia in a human or non-human mammal comprising administering a therapeutically effective amount of the compound of claim 1 to the human or non-human mammal.

11. A method for inducing sedation or hypnosis in a human or non-human mammal comprising administering a therapeutically effective amount of the compound claim 1 to the human or non-human mammal.

12. A method for inducing anesthesia in a human or non-human mammal comprising administering a therapeutically effective amount of the compound of claim 1 to the human or non-human mammal.

13. A method for modulating the necessary time to induce sleep and its duration in a human or non-human mammal comprising administering a therapeutically effective amount of the compound of claim 1 to the human or non-human mammal.

14. A method for inducing muscle relaxation in a human or non-human mammal comprising administering a therapeutically effective amount of the compound of claim 1 to the human or non-human mammal.

15. A pharmaceutical composition comprising a therapeutically effective amount of the compound as defined in claim 1 or a pharmaceutically acceptable salt, polymorph, hydrate, tautomer, solvate, or stereoisomer thereof, together with an appropriate amount of a pharmaceutical excipient or carrier.

* * * * *